United States Patent [19]

Esanu

[11] Patent Number: 4,704,454
[45] Date of Patent: Nov. 3, 1987

[54] PYRANODERIVATIVES, THEIR PREPARATION AND THERAPEUTIC COMPOSITIONS CONTAINING THE SAME

[75] Inventor: André Esanu, Paris, France

[73] Assignee: Societe de Conseils de Recherches et d'Applications Scientifiques, Paris, France

[21] Appl. No.: 718,064

[22] Filed: Apr. 1, 1985

[30] Foreign Application Priority Data

Apr. 24, 1984 [GB] United Kingdom ................ 8410484

[51] Int. Cl.$^4$ ...................... A61K 31/70; C07H 17/00; C07H 19/06
[52] U.S. Cl. ........................................ 536/24; 536/23; 536/26
[58] Field of Search ...................... 536/23, 24, 26, 28; 514/43, 46, 44, 42

[56] References Cited

U.S. PATENT DOCUMENTS 3,868,361 2/1975 Tolman et al. ...................... 536/28
4,590,180 5/1986 Irmscher et al. ................... 536/26

Primary Examiner—Ronald W. Griffin
Attorney, Agent, or Firm—Lucas & Just

[57] ABSTRACT

This invention relates to new pyranoderivatives of the formula:

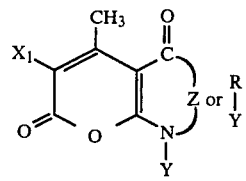

wherein $X_1$ is H, Cl or Br and Z stands for:

I      II

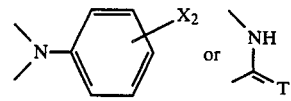

wherein $X_2$ is H, Cl or Br, T is O or S and Y stands for an arabinose, xylose or ribose moiety, the acetylated form of the same, with either a pyranose or furanose configuration and bound to the R moiety of either the α or the β anomer, to a preparation process of said compounds from stoichiometric proportions of the compound R—H and of the selected ose, and to therapeutic compositions, the active ingredient of which comprises at least one of these compounds associated with an appropriate diluent or carrier.

4 Claims, No Drawings

PYRANODERIVATIVES, THEIR PREPARATION AND THERAPEUTIC COMPOSITIONS CONTAINING THE SAME

The present invention relates to new pyranoderivatives, of the formula:

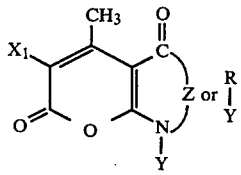

wherein $X_1$ is H, Cl or Br and Z stands for:

I      II

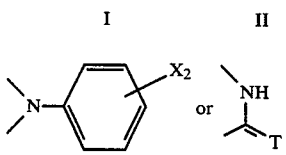

wherein $X_2$ is H, Cl or Br, T is O or S and Y stands for an arabinose, xylose or ribose moiety, the acetylated form of the same, with either a pyranose or furanose configuration and bound to the R moiety of either the α or the β anomer.

These compounds are more particularly interesting for their therapeutic action in the field of virus- and bacteria-induced diseases and, for some of them, for their activity of the cardio-vascular field.

The invention relates also to a preparation process of these compounds consisting in reacting, in acetonitrile, at room temperature and under nitrogen circulation, stoichiometric proportions of the compound R—H and of the selected ose, under its acetylated form, in the presence of 1,1,1,3,3,3-hexamethyldisilazane, trimethylchlorosilane and tin tetrachloride; the reaction is performed under stirring for 12 to 24 hours.

The invention relates, finally, to therapeutic compositions the active ingredient of which comprises at least one compound of the invention, associated with an appropriate diluent or carrier.

This leads to the acetylated form of the compounds of the invention; the corresponding non-acetylated compounds are obtained by the usual desacetylation techniques.

As to the starting material:

A—The acetylated oses are obtained from the corresponding oses, by acetylation, as usual, by an excess of acetic anhydride in the presence of perchloric acid, under stirring at room temperature (0.5 to one hour). The reaction mixture is poured on icy water, which gives an oily product, extracted by chloroform and dried. The evaporation of chloroform under reduced pressure leads to an oil with a yield of about 55 to 85% according to the product. As these oses exist under pyranose and furanose form, each of these forms or their mixtures in various proportions may be used.

B—The various condensed ring RH are obtained as follows:

(a) Z is I: RH=c

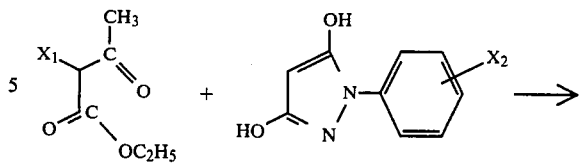

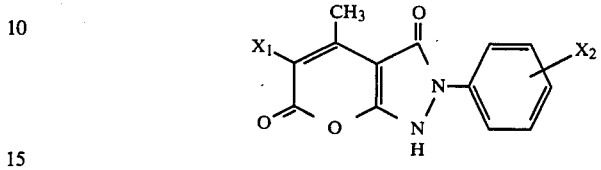

For the compound in which both X are H, 123 g of 1-phenyl-3,5-dihydroxypyrazole (0.7 mol) are treated by 0.2 l of ethyl acetylacetate (2.1 mol) at 130° C. After distillation of water and ethanol produced by the reaction, the temperature raises up to 180° C. After 3 hours, the mixture is cooled, poured in a boiling mixture of water and ethanol (50/50), which leads to a suspension. The suspension is stirred, fittered, washed by 0.1 l of a 50/50 water and methanol mixture, dried under reduced pressure and recrystallized in ethyleneglycol monomethylic ether; yield 105 g (73%).

The process is the same when any of the X (or both) stands for an halogen atom.

(b) Z is II: RH=d

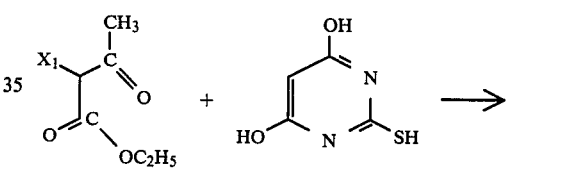

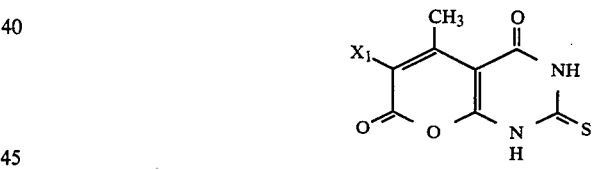

The process is the same as in (a) above but starting with 100 g (0.7 mol) of thiobarbituric acid. Yield 101 g (68%). Barbituric acid is used for T=O.

Accordingly, the starting material RH is:

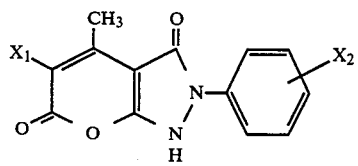

or

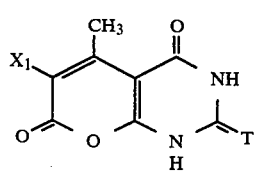

with $X_1$ and $X_2$=H, Cl or Br, T=S or O.

The invention will be better understood from the following examples. As the process is strictly the same for all the compounds, only the first example will be described in details; for the other examples, only starting materials and characteristics will be given.

EXAMPLE C: RH=c (1)

N-1-($\beta$-D-2,3,5-tri-O-acetylribofuranosyl)-2-phenyl-4-methyl pyrano-(2,3-c)-pyrazole-3,6-dione $X_1 = X_2 = H$
$\beta$-D-ribofuranose In a one liter reactor fitted with stirring means are poured, under nitrogen circulation, 19.4 g (0.08 mol) of 2-phenyl-4-methyl-pyrano-(2,3-c)-pyrazole-3,6-dione, 12.3 ml (0.0585 mol) of hexamethyldisilazane, 27.3 ml (0.0215 mol) of tetramethylchlorosilane, 18.7 ml (0.16 mol) of $SnCl_4$ and 250 ml of acetonitrile; after stirring, there is obtained a a solution to which are added 25.5 g (0.08 mol) of $\beta$-D-tetraacetyl-ribofuranose. Stirring is maintained for 19 hours under nitrogen circulation. The reacting mixture is then poured on a cold 10% $NaHCO_3$ solution and pH is adjusted to 6.7; 320 ml of $CHCl_3$ are added under stirring and the organic phase is separated, washed with water, dried by sodium sulfate and evaporated to dryness. The dry product is then triturated with diethyl ether and recrystallized by hot ethanol. After separation, washing and drying, there is obtained 12.4 g (yield 31%) of a white crystalline powder, the analysis of which shows a good correspondence with the formula $C_{24}H_{25}N_2O_{10}$. Melting point 157° C. (Tottoli). This compound is insoluble in water and soluble in dimethylsulfoxide.

The corresponding desacetylated product (formula $C_{18}H_{19}N_2O_7$) is a white powder melting at 173°-175° C. (Tottoli), insoluble in water and soluble in dimethylsulfoxide.

(2)

N-1-($\beta$-D-2,3,5-tri-O-acetylribofuranosyl)-2-phenyl-4-methyl-5-chloro-pyrano-(2,3-c)-pyrazole-3,6-dione $X_1 = H$
$X_2 = Cl$
$\beta$-D-ribofuranose Reaction time 15 hours—Yield 36.5% of a white crystalline product melting at 168° C. (Tottoli). Insoluble in water, soluble in dimethylsulfoxide. Analysis shows a perfect correspondence with the formula $C_{24}H_{24}N_2O_{10}Cl$.

The corresponding desacetylated product (formula $C_{18}H_{18}N_2O_7Cl$) is a beige powder melting at 189° C. (Tottoli), insoluble in water and soluble in dimethylsulfoxide.

(3)

N-1-($\beta$-D,2,3,5-tri-O-acetylribofuranosyl)-2-p-chlorophenyl-4-methyl-5-chloro-pyrano-(2,3-c)-pyrazole-3,6-dione $X_1 = X_2 = Cl$
$\beta$-D-ribofuranose Reaction time 12 hours—Yield 38% of a white crystalline powder melting at 193° C. (Tottoli). Insoluble in water, soluble in dimethylsulfoxide. Analysis shows a perfect correspondence with the formula $C_{24}H_{23}N_2O_{10}Cl_2$.

The corresponding desacetylated product (formula $C_{18}H_{17}N_2O_7Cl_2$) is a beige powder melting at 233° C. (Tottoli), insoluble in water and soluble in dimethylsulfoxide.

(4)

N-1-($\beta$-D-2,3,4-tri-O-acetylxylopyranosyl)-2-phenyl-4-methyl pyrano-(2,3-c)-pyrazole-3,6-dione $X_1 = X_2 = H$
$\beta$-D-xylopyranose Reaction time 17 hours—Yield 39% of a white crystalline powder melting at 201° C. (Tottoli). Insoluble in water, soluble in dimethylsulfoxide. Analysis shows a perfect correspondence with the formula $C_{24}H_{25}N_2O_{10}$.

The corresponding desacetylated product (formula $C_{18}H_{19}N_2O_7$) is a beige powder melting at 246° C. (Tottoli), insoluble in water and soluble in dimethylsulfoxide.

(5)

N-1-($\beta$-D-2,3,5-tri-O-acetylxylofuranosyl)-2-phenyl-4-methyl pyrano-(2,3-c)-pyrazole-3,6-dione $X_1 = X_2 - H$
$\beta$-D-xylofuranose Reaction time 22 hours—Yield 29.5% of a white crystalline product melting at 168° C. (Tottoli). Insoluble in water, soluble in dimethylsulfoxide. Analysis shows a perfect correspondence with the formula $C_{24}H_{25}N_2O_{10}$.

The corresponding desacetylated product (formula $C_{18}H_{19}N_2O_7$) is a beige powder melting at 218° C. (Tottoli). Insoluble in water and soluble in dimethylsulfoxide.

(6)

N-1-($\beta$-D-2,3,5-tri-O-acetylxylofuranosyl)-2-p-bromophenyl-4-methyl-pyrano-(2,3-c)-pyrazole-3,6-dione $X_1 = H$
$X_2 = Br$
$\beta$-D-xylofuranose Reaction time 16 hours—Yield 27% of a white crystalline powder melting at 159° C. (Tottoli). Insoluble in water, soluble in dimethylsulfoxide. Analysis shows a perfect correspondence with the formula $C_{24}H_{24}N_2O_{10}Br$.

The corresponding desacetylated product (formula $C_{18}H_{18}N_2O_7Br$) is a beige powder melting at 241° C. (Tottoli). Insoluble in water and soluble in dimethylsulfoxide.

(7)

N-1-($\beta$-D-2,3,4-tri-O-acetylxylopyranosyl)-2-phenyl-4-methyl-5-chloro-pyrano-(2,3-c)-pyrazole-3,6-dione $X_1 = Cl$
$X_2 = H$
$\beta$-D-xylopyranose Reaction time 23 hours—Yield 42% of a white crystalline product melting at 188° C. (Tottoli). Poorly soluble in water, soluble in dimethylsulfoxide. Analysis shows a perfect correspondence with the formula $C_{24}H_{24}N_2O_{10}Cl$. The corresponding desacetylated product (formula $C_{18}N_{18}N_2O_7Cl$) is a beige powder melting at 262° C. (Tottoli). Insoluble in water and soluble in dimethylsulfoxide.

(8)

N-1-(D-2,3,5-tri-O-acetylarabinofuranosyl)-2-phenyl-4-methyl-pyrano-(2,3-c)-pyrazole-3,6-dione $X_1 = X_2 = H$
D-arabinofuranose Reaction time 17 hours—Yield 28% of a white crystalline product melting at 144° C. (Tottoli). Insoluble in water, soluble in dimethylsulfoxide. Analysis shows a perfect correspondence with the formula $C_{24}H_{25}N_2O_{10}$.

The corresponding desacetylated product (formula $C_{18}H_{19}N_2O_7$) is a beige powder melting at 244° C. (Tottoli). Insoluble in water and soluble in dimethylsulfoxide.

(9)

N-1-(D-2,3,5-tri-O-acetylarabinofuranosyl)-2-p-chlorophenyl-4-methyl-pyrano-(2,3-c)-pyrazole-3,6-dione $X_1 = H$
$X_2 = Cl$
D-arabinofuranose Reaction time 17 hours—Yield 39% of a white crystalline product melting at 177° C. (Tottoli). Insoluble in water, soluble in dimethylsulfoxide. Analysis shows a perfect correspondence with the formula $C_{24}H_{24}N_2O_{10}Cl$.

The corresponding desacetylated product (formula $C_{18}H_{18}N_2O_7Cl$) is a beige powder melting at 201° C. (Tottoli). Insoluble in water and soluble in dimethylsulfoxide.

(10)

N-1-α-D-2,3,5-tri-O-acetylarabinofuranosyl)-2-p-chlorophenyl-4-methyl-pyrano-(2,3-c)-pyrazole-3,6-dione $X_1 = H$
$X_2 = Cl$
α-D-arabinofuranose Reaction time 18 hours—Yield 32.5% of a white-grey crystalline powder melting at 189° C. Tottoli). Insoluble in water, soluble in dimethylsulfoxide. Analysis shows a perfect correspondence with the formula $C_{24}H_{24}N_2O_{10}Cl$.

The corresponding desacetylated product (formula $C_{18}H_{18}N_2O_7Cl$) is a beige powder melting at 249° C. Tottoli). Insoluble in water and soluble in dimethylsulfoxide.

EXAMPLE D: RH=d (1)

N-1-(β-D-2,3,5-tri-O-acetylarabinofuranosyl)-5-methyl-1,2,3,4-tetrahydro-7H-pyrano-(2,3-d)-pyrimidine-2,4,7-trione $X_2 = H$
$T = O$
β-D-arabinofuranose Reaction time 22 hours—Yield 33% of a white crystalline powder melting at 190° C. (Tottoli). Insoluble in water, soluble in dimethylsulfoxide. Analysis shows a perfect correspondence with the formula $C_{19}H_{20}N_2O_{11}$.

The corresponding desacetylated product (formula $C_{13}H_{14}N_2O_8$) is a beige powder melting at 210°–212° C. (Tottoli). Insoluble in water and soluble in dimethylsulfoxide.

(2)

N-1-(β-D-2,3,5-tri-O-acetylarabinofuranosyl)-5-methyl-6-chloro-1,2,3,4-tetrahydro-7H-pyrano-(2,3-d)-pyrimidine-2,4,7-trione $X_1 = Cl$
$T = O$
β-D-arabinofuranose Reaction time 13 hours—Yield 29.5% of a white crystalline product melting at 203° C. (Tottoli). Insoluble in water, soluble in dimethylsulfoxide. Analysis shows a good correspondence with the formula $C_{19}H_{19}N_2O_{11}Cl$.

The corresponding desacetylated product (formula $C_{13}H_{13}N_2O_8Cl$) is a beige powder melting at 255° C. (Tottoli). Insoluble in water and in dimethylsulfoxide.

(3)

N-1-(β-D-2,3,5-tri-O-acetylarabinofuranosyl)-5-methyl-6-bromo-1,2,3,4-tetrahydro-7H-pyrano-(2,3-d)-pyrimidine-2,4,7-trione $X_1 = Br$
$T = O$
β-D-arabinofuranose Reaction time 17 hours—Yield 26% of a white crystalline product melting at 180° C. (Tottoli). Insoluble in water, soluble in dimethylsulfoxide. Analysis shows a good correspondence with the formula $C_{19}H_{19}N_2O_{11}Br$.

The corresponding desacetylated product (formula $C_{13}H_{13}N_2O_8Br$) is a beige powder melting at 222° C. (Tottoli). Insoluble in water and in dimethylsulfoxide.

(4)

N-1-(β-D-2,3,4-tri-O-acetylarabinopyranosyl)-5-methyl-1,2,3,4-tetrahydro-7H-pyrano-(2,3-d)-pyrimidine-2,4,7-trione $X_1 = H$
$T = O$
β-D-arabinopyranose Reaction time 18 hours—Yield 41% of a white crystalline powder melting at 175° C. (Tottoli). Insoluble in water, soluble in dimethylsulfoxide. Analysis shows a good correspondence with the formula $C_{19}H_{20}N_2O_{11}$.

The corresponding desacetylated product (formula $C_{13}H_{14}N_2O_8$) is a beige powder melting at 218° C. (Tottoli). Insoluble in water and soluble in dimethylsulfoxide.

(5)

N-1-(D-2,3,5-tri-O-acetylarabinofuranosyl)-5-methyl-1,2,3,4-tetrahydro-7H-pyrano-(2,3-d)-pyrimidine-4,7-dione-2-thioxo $X_1 = H$
$T = S$
D-arabinofuranose Reaction time 20 hours—Yield 36% of a powder melting at 202° C. (Tottoli). Insoluble in water, soluble in dimethylsulfoxide. Analysis shows a perfect correspondence with the formula $C_{19}H_{20}N_2O_{10}S$.

The corresponding desacetylated product (formula $C_{13}H_{14}N_2O_7S$) is a beige powder melting at 184° C. (Tottoli). Insoluble in water and soluble in dimethylsulfoxide.

(6)

N-1-(α-D-2,3,5-tri-O-acetylarabinofuranosyl)-5-methyl-1,2,3,4-tetrahydro-7H-pyrano-(2,3d)-pyrimidine-4,7-dione-2-thioxo $X_1 = H$
$T = S$
α-D-arabinofuranose Reaction time 20 hours—Yield 24.5% of a white crystalline powder melting at 165° C. (Tottoli). Insoluble in water, soluble in dimethylsulfoxide. Analysis shows a good correspondence with the formula $C_{19}H_{20}N_2O_{10}S$.

The corresponding desacetylated product (formula $C_{13}H_{14}N_2O_7S$) is a beige powder melting at 242° C. (Tottoli). Insoluble in water and soluble in dimethylsulfoxide.

(7)

N-1-(α-D-2,3,5-tri-O-acetylarabinofuranosyl)-5-methyl-6-chloro-1,2,3,4-tetrahydro-7H-pyrano-(2,3-d)-pyrimidine-4,7-dione-2-thioxo $X_1 = Cl$
$T = S$
α-D-arabinofuranose Reaction time 15 hours—Yield 36.5% of a white crystalline powder melting at 194° C. (Tottoli). Insoluble in water, soluble in dimethylsulfoxide. Analysis shows a perfect correspondence with the formula $C_{19}H_{19}N_2O_{10}SCl$.

The corresponding desacetylated product (formula $C_{13}H_{13}N_2O_7SCl$) is a beige powder melting at 229° C. (Tottoli). Insoluble in water and soluble in dimethylsulfoxide.

(8)

N-1-(α-D-2,3,4-tri-O-acetylarabinopyranosyl)-5-methyl-1,2,3,4-tetrahydro-7H-pyrano-(2,3d)-pyrimidine-4,7-dione-2-thioxo $X_1 = H$
$T = S$
α-D-arabinopyranose Reaction time 19 hours—Yield 36% of a white-grey crystalline powder melting at 230° C. (Tottoli). Insoluble in water, soluble in dimethylsulfoxide. Analysis shows a good correspondence with the formula $C_{19}H_{20}N_2O_{10}S$.

The corresponding desacetylated product (formula $C_{13}H_{14}N_2O_7S$) is a beige powder melting at 207°-209° C. (Tottoli). Insoluble in water and soluble in dimethylsulfoxide.

(9)

N-1-(β-D-2,3,4-tri-O-acetylarabinopyranosyl)-5-methyl-1,2,3,4-tetrahydro-7H-pyrano-(2,3-d)-pyrimidine-4,7-dione-2-thioxo $X_1 = H$
$T = S$
β-D-arabinopyranose Reaction time 21 hours—Yield 34% of a white crystalline powder melting at 226° C. (Tottoli). Insoluble in water, soluble in dimethylsulfoxide. Analysis shows a good correspondence with the formula $C_{19}H_{20}N_2O_{10}S$.

The corresponding desacetylated product (formula $C_{13}H_{14}N_2O_7S$) is a beige powder melting at 248° C. (Tottoli). Insoluble in water and soluble in dimethylsulfoxide.

(10)

N-1-(D-2,3,4-tri-O-acetylarabinopyranosyl)-5-methyl-1,2,3,4-tetrahydro-7H-pyrano-(2,3d)-pyrimidine-4,7-dione-2-thioxo $X_1 = H$ $T = S$
D-arabinopyranose Reaction time 23 hours—Yield 44% of a crystalline powder melting at 163° C. (Tottoli). Insoluble in water, soluble in dimethylsulfoxide. Analysis shows a perfect correspondence with the formula $C_{19}H_{20}N_2O_{10}S$.

The corresponding desacetylated product (formula $C_{13}H_{14}N_2O_7S$) is a beige powder melting at 239° C. (Tottoli). Insoluble in water and soluble in dimethylsulfoxide.

(11)

N-1-(D-2,3,4-tri-O-acetylarabinopyranosyl)-5-methyl-6-chloro-1,2,3,4-tetrahydro-7H-pyrano-(2,3d)-pyrimidine-4,7-dione-2-thioxo $X_1 = Cl$
$T = S$
D-arabinopyranose Reaction time 22 hours—Yield 30.5% of a pale yellow crystalline powder melting at 193° C. (Tottoli). Insoluble in water, soluble in dimethylsulfoxide. Analysis shows a perfect correspondence with the formula $C_{19}H_{19}N_2O_{10}SCl$.

The corresponding desacetylated product (formula $C_{13}H_{13}N_2O_7SCl$) is a beige powder melting at 235° C. (Tottoli). Insoluble in water and soluble in dimethylsulfoxide.

(12)

N-1-(α+β-D-2,3,4-tri-O-acetylarabinopyranosyl)-5-methyl-1,2,3,4-tetrahydro-7H-pyrano-(2,3-d)-pyrimidine-4,7-dione-2-thioxo $X_1 = H$
$T = S$
α+β-D-arabinopyranose (commercial product)

Reaction time 20 hours—Yield 39.5% of a pale yellow crystalline powder melting at 214° C. (Tottoli). Insoluble in water, soluble in dimethylsulfoxide. Analysis shows a good correspondence with the formula $C_{19}H_{20}N_2O_{10}S$.

The corresponding desacetylated product (formula $C_{13}H_{14}N_2O_7S$) is a beige powder melting at 241° C. (Tottoli). Insoluble in water and soluble in dimethylsulfoxide.

(13)

N-1-(β-D-2,3,5-tri-O-acetylribofuranosyl)-5-methyl-1,2,3,4-tetrahydro-7H-pyrano-(2,3d)-pyrimidine-2,4,7-trione $X_1 = H$
$T = O$
β-D-ribofuranose Reaction time 18 hours—Yield 26% of a white crystalline powder melting at 165° C. (Tottoli). Insoluble in water, soluble in dimethylsulfoxide. Analysis shows a perfect correspondence with the formula $C_{19}H_{20}N_2O_{11}$.

The corresponding desacetylated product (formula $C_{13}H_{14}N_2O_8$) is a beige powder melting at 249° C. (Tottoli). Insoluble in water and soluble in dimethylsulfoxide.

(14)

N-1-(β-D-2,3,5-tri-O-acetylribofuranosyl)-5-methyl-6-chloro-1,2,3,4-tetrahydro-7H-pyrano-(2,3d)-pyrimidine-2,4,7-trione $X_1 = Cl$
$T = O$
β-D-ribofuranose Reaction time 15 hours—Yield 32% of a white crystalline product melting at 208° C. (Tottoli). Insoluble in water, soluble in dimethylsulfoxide. Analysis shows a perfect correspondence with the formula $C_{19}H_{19}N_2O_{11}Cl$.

The corresponding desacetylated product (formula $C_{13}H_{13}N_2O_8Cl$) is a beige powder melting at 199° C. (Tottoli). Insoluble in water and soluble in dimethylsulfoxide.

(15)

N-1-(β-D-2,3,5-tri-O-acetylribofuranosyl)-5-methyl-6-bromo-1,2,3,4-tetrahydro-7H-pyrano-(2,3-d)-pyrimidine-2,4,7-trione $X_1 = Br$
$T = O$
β-D-ribofuranose Reaction time 16 hours—Yield 31% of a white crystalline product melting at 271° C. (Tottoli). Insoluble in water, soluble in dimethylsulfoxide. Analysis shows a good correspondence with the formula $C_{19}H_{19}N_2O_{11}Br$.

The corresponding desacetylated product (formula $C_{13}H_{13}N_2O_8Br$) is a beige powder melting at 260° C. (Tottoli). Insoluble in water and soluble in dimethylsulfoxide.

(16)

N-1-(β-D-2,3,4-tri-O-acetylribopyranosyl)-5-methyl-1,2,3,4-tetrahydro-7H-pyrano-(2,3-d)-pyrimidine-2,4,7-trione $X_1 = H$
$T = O$
β-D-ribopyranose Reaction time 14 hours—Yield 38% of a white powder melting at 123° C. (Tottoli). Insoluble in water, soluble in dimethylsulfoxide. Analysis shows a perfect correspondence with the formula $C_{19}H_{20}N_2O_{11}$.

The corresponding desacetylated product (formula $C_{13}H_{14}N_2O_8$) is a beige powder melting at 190° C. (Tottoli). Insoluble in water and soluble in dimethylsulfoxide.

(17)

N-1-(β-D-2,3,4-tri-O-acetylribopyranosyl)-5-methyl-6-bromo-1,2,3,4-tetrahydro-7H-pyrano-(2,3d)-pyrimidine-2,4,7-trione $X_1 = Br$
$T = O$
β-D-ribopyranose Reaction time 21 hours—Yield 24% of a white crystalline powder melting over 300° C. (Tottoli). Insoluble in water, soluble in dimethylsulfoxide. Analysis shows a good correspondence with the formula $C_{19}H_{19}N_2O_{11}Br$.

The corresponding desacetylated product (formula $C_{13}H_{13}N_2O_8Br$) is a beige powder melting at 255° C. (Tottoli). Insoluble in water and soluble in dimethylsulfoxide.

(18)

N-1-(α-D-2,3,4-tri-O-acetylribopyranosyl)-5-methyl-1,2,3,4-tetrahydro-7H-pyrano-(2,3-d)-pyrimidine-2,4,7-trione $X_1 = H$
$T = O$
α-D-ribopyranose Reaction time 22 hours—Yield 33% of a white crystalline powder melting at 172° C. (Tottoli). Insoluble in water, soluble in dimethylsulfoxide. Analysis shows a good correspondence with the formula $C_{19}H_{20}N_2O_{11}$.

The corresponding desacetylated product (formula $C_{13}H_{14}N_2O_8$) is a beige powder melting at 233° C. (Tottoli). Insoluble in water, soluble in dimethylsulfoxide.

(19)

N-1-(D-2,3,5-tri-O-acetylribofuranosyl)-5-methyl-1,2,3,4-tetrahydro-7H-pyrano-(2,3-d)-pyrimidine-4,7-dione-2-thioxo $X_1 = H$
$T = S$
D-ribofuranose Reaction time 20 hours—Yield 43% of a white crystalline powder melting at 188° C. (Tottoli). Insoluble in water and soluble in dimethylsulfoxide. Analysis shows a perfect correspondence with the formula $C_{19}H_{20}N_2O_{10}S$.

The corresponding desacetylated product (formula $C_{13}H_{14}N_2O_7S$) is a beige powder melting at 212° C. (Tottoli). Insoluble in water and soluble in dimethylsulfoxide.

(20)

N-1-(β-D-2,3,5-tri-O-acetylribofuranosyl)-5-methyl-1,2,3,4-tetrahydro-7H-pyrano-(2,3-d)-pyrimidine-4,7-dione-2-thioxo $X_1 = H$
$T = S$
β-D-ribofuranose Reaction time 15 hours—Yield 40% of a white crystalline powder melting at 295° C. (Tottoli). Insoluble in water, soluble in dimethylsulfoxide. Analysis shows a perfect correspondence with the formula $C_{19}H_{20}N_2O_{10}S$.

The corresponding desacetylated product (formula $C_{13}H_{14}N_2O_7S$) is a beige powder melting at 260° C. (Tottoli). Insoluble in water and soluble in dimethylsulfoxide.

(21)

N-1-(α-D-2,3,5-tri-O-acetylribofuranosyl)-5-methyl-1,2,3,4-tetrahydro-7H-pyrano-(2,3-d)-pyrimidine-4,7-dione-2-thioxo $X_1 = H$
$T = S$
α-D-ribofuranose Reaction time 19 hours—Yield 37% of a white crystalline powder melting at 276° C. (Tottoli). Insoluble in water, soluble in dimethylsulfoxide. Analysis shows a good correspondence with the formula $C_{19}H_{20}N_2O_{10}S$.

The corresponding desacetylated product (formula $C_{13}H_{14}N_2O_7S$) is a beige powder melting at 236° C. (Tottoli). Insoluble in water and soluble in dimethylsulfoxide.

(22)

N-1-(D-2,3,4-tri-O-acetylribopyranosyl)-5-methyl-1,2,3,4-tetrahydro-7H-pyrano-(2,3-d)-pyrimidine-4,7-dione-2-thioxo $X_1 = H$
$T = S$
D-ribopyranose Reaction time 17 hours—Yield 27% of a white crystalline powder melting at 215° C. (Tottoli). Insoluble in water, soluble in dimethylsulfoxide. Analysis shows a perfect correspondence with the formula $C_{19}H_{20}N_2O_{10}S$.

The corresponding desacetylated product (formula $C_{13}H_{14}N_2O_7S$) is a white powder melting at 260° C. (Tottoli). Insoluble in water and soluble in $NaHCO_3$.

(23)
N-1-(α-D-2,3,4-tri-O-acetylribopyranosyl)-5-methyl-1,2,3,4-tetrahydro-7H-pyrano-(2,3-d)-pyrimidine-4,7-dione-2-thioxo $X_1=H$
$T=S$
α-D-ribopyranose Reaction time 22 hours—Yield 34% of a white crystalline powder melting at 233° C. (Tottoli). Insoluble in water, soluble in dimethylsulfoxide. Analysis shows a perfect correspondence with the formula $C_{19}H_{20}N_2O_{10}S$.

The corresponding desacetylated product (formula $C_{13}H_{14}N_2O_7S$) is a white powder melting at 174° C. (Tottoli). Insoluble in water and soluble in $NaHCO_3$.

(24)
N-1-(β-D-2,3,4-tri-O-acetylribopyranosyl)-5-methyl-1,2,3,4-tetrahydro-7H-pyrano-(2,3-d)-pyrimidine-4,7-dione-2-thioxo $X_1=H$
$T=S$
β-D-ribopyranose Reaction time 21 hours—Yield 37% of a white crystalline powder melting at 199° C. (Tottoli). Insoluble in water, soluble in dimethylsulfoxide. Analysis shows a good correspondence with the formula $C_{19}H_{20}N_2O_{10}S$.

The corresponding desacetylated product (formula $C_{13}H_{14}N_2O_7S \cdot H_2O$) is a white crystalline powder melting at 280° C. Tottoli). Insoluble in water and soluble in $NaHCO_3$.

(25)
N-1-(β-D-2,3,5-tri-O-acetylxylofuranosyl)-5-methyl-1,2,3,4-tetrahydro-7H-pyrano-(2,3-d)-pyrimidine-2,4,7-trione $X_1=H$
$T=O$
β-D-xylofuranose Reaction time 17 hours—Yield 28% of a pale yellow crystalline powder melting at 218° C. (Tottoli). Insoluble in water, soluble in dimethylsulfoxide. Analysis shows a perfect correspondence with the formula $C_{19}H_{20}N_2O_{11}$.

The corresponding desacetylated product (formula $C_{13}H_{14}N_2O_8$) is a beige powder melting at 249° C. (Tottoli). Insoluble in water and soluble in dimethylsulfoxide.

(26)
N-1-(β-D-2,3,5-tri-O-acetylxylofuranosyl)-5-methyl-6-chloro-1,2,3,4-tetrahydro-7H-pyrano-(2,3-d)-pyrimidine-2,4,7-trione $X_1=Cl$
$T=O$
β-D-xylofuranose Reaction time 19 hours—Yield 26% of a pale yellow product melting at 247° C. (Tottoli). Insoluble in water, soluble in dimethylsulfoxide. Analysis shows a good correspondence with the formula $C_{19}H_{19}N_2O_{11}Cl$.

The corresponding desacetylated product (formula $C_{13}H_{13}N_2O_8Cl$) is a beige powder melting at 208° C. (Tottoli). Insoluble in water and in dimethylsulfoxide.

(27)
N-1-(β-D-2,3,4-tri-O-acetylxylopyranosyl)-5-methyl-1,2,3,4-tetrahydro-7H-pyrano-(2,3-d)-pyrimidine-2,4,7-trione $X_1=H$
$T=O$
β-D-xylopyranose Reaction time 22 hours—Yield 34% of a yellow powder melting at 270° C. (Tottoli). Insoluble in water, soluble in dimethylsulfoxide. Analysis shows a good correspondence with the formula $C_{19}H_{20}N_2O_{11}$.

The corresponding desacetylated product (formula $C_{13}H_{14}N_2O_8$) is a beige powder melting at 243° C. (Tottoli). Insoluble in water and soluble in dimethylsulfoxide.

(28)
N-1-(α-D-2,3,5-tri-O-acetylxylofuranosyl)-5-methyl-1,2,3,4-tetrahydro-7H-pyrano-(2,3-d)-pyrimidine-4,7-dione-2-thioxo $X_1=H$
$T=S$
α-D-xylofuranose Reaction time 20 hours—Yield 29% of a white crystalline powder melting at 202° C. (Tottoli). Insoluble in water, soluble in dimethylsulfoxide. Analysis shows a good correspondence with the formula $C_{19}H_{20}N_2O_{10}S$.

The corresponding desacetylated product (formula $C_{13}H_{14}N_2O_7S$) is a beige powder melting at 234° C. (Tottoli). Insoluble in water and soluble in dimethylsulfoxide.

(29)
N-1-(D-2,3,5-tri-O-acetylxylofuranosyl)-5-methyl-1,2,3,4-tetrahydro-7H-pyrano-(2,3-d)-pyrimidine-4,7-dione-2-thioxo $X_1=H$
$T=S$
D-xylofanose Reaction time 19 hours—Yield 30% of a powder melting at 222° C. (Tottoli). Insoluble in water, soluble in dimethylsulfoxide. Analysis shows a perfect correspondence with the formula $C_{19}H_{20}N_2O_{10}S$.

The corresponding desacetylated product (formula $C_{13}H_{14}N_2O_7S$) is a beige powder melting at 255° C. (Tottoli). Insoluble in water and soluble in dimethylsulfoxide.

(30)
N-1-(β-D-2,3,4-tri-O-acetylxylopyranosyl)-5-methyl-1,2,3,4-tetrahydro-7H-pyrano-(2,3-d)-pyrimidine-4,7-dione-2-thioxo $X_1=H$
$T=S$
β-D-xylopyranose Reaction time 22 hours—Yield 31% of a white crystalline powder melting at 221° C. (Tottoli). Insoluble in water, soluble in dimethylsulfoxide. Analysis shows a good correspondence with the formula $C_{19}H_{20}N_2O_{10}S$.

The corresponding desacetylated product (formula $C_{13}H_{14}N_2O_7S$) is a beige powder melting at 260° C. (Tottoli). Insoluble in water and soluble in dimethylsulfoxide.

TOXICITY

Preliminary toxicity studies per os on rats and mice have not revealed any toxicity at 650 mg/kg for any of the compounds. As maximum efficient therapeutic doses are of about 50 mg/kg, slightly varying with the compounds, higher doses have not been tested.

PHARMACOLOGY

I Effect of Topical Treatment with the Compounds of the Invention on Genital Infections of Guinea Pigs Groups of each 4 white guinea pigs aged 3–4 months and weighing approximately 200 gms were inoculated vaginally with cotton wool swabs impregnated with either WAL strain of HSV-1 ($10^{7.5}$ pfu/ml) or 333 strain of HSV-2 ($10^{7.3}$ pfu/ml); swabs soaked in virus were rubbed on to the external surfaces and implanted internally into the vagina. Twentyfour hours following virus inoculation, the animals were divided into 18 groups and 17 were treated with either 15 of the compounds of the invention (1.5% in cream base), Acyclovir as obtained commercially, or cream base placebo: the 18th group (control) were not treated. Treatments were given four times a day throughout the observation period of 11 days. Animals were examined daily for clinical evidence of HSV infection; these included erythema, exudate, a combination of erythema and exudate and urine retention which is a common feature in the latter part of the HSV infection. Previous studies had shown that genital infection with HSV-1 (WAL strain) or HSV-2 (333 strain) produced erythema and exudate without necessarily producing vesicles.

The results are reported in Table 1, central portion, showing a clinical score on days; in this table, the compounds are identified by the number of their example as such for the acetylated form or followed by (OH) for the desacetylated form. Observations of clinical reactions were made on days 1–11 after virus inoculations. For HSV-1 infected control animals, no reactions were seen until day 6 post-inoculation; at this time extensive erythema and exudate was observed and this continued to day 11 when urine retention was found: this course of infection usually precedes fatal encephalitis, but the experiments were not allowed to proceed to this end. Animals treated with placebo cream showed similar reactions to those found in untreated animals (control). In contrast, animals treated with the compounds of the invention and Acyclovir showed delayed onset of erythema and minimal exudate in the period 7–11 days following virus inoculation. The results indicate clinical amelioration of the symptoms of genital HSV-1 infection in guinea pigs by the compounds of the invention and Acyclovir.

The clinical events for animals inoculated with HSV-2 and treated with antiviral compounds were more clear cut. Thus, uninoculated controls and placebo treated animals developed erythema and/or exudate from days 6–7 following virus inoculation, and urine retention was observed on days 10–11. In contrast, no erythema or exudate was observed in animals treated with either Acyclovir and little with the compounds of the invention.

The results are shown in same Table 1, right hand portion. From these figures it clearly appears that, compared to Acyclovir, the compounds of the invention have a quite similarl activity on HSV-2 viruses but a superior activity on HSV-1 viruses.

TABLE 1

| COMPOUNDS | HSV-1 (WAL) | | | | | HSV-2 (333) | | | | |
|---|---|---|---|---|---|---|---|---|---|---|
| | \multicolumn{10}{c}{Clinical score on days} |
| | 7 | 8 | 9 | 10 | 11 | 7 | 8 | 9 | 10 | 11 |
| Placebo | 2 | 2 | 2 | 2 | 2 | 3 | 3 | 3 | 2R | 2R |
| Acyclovir | 2 | 1 | 2 | 1 | 1 | — | — | — | — | — |
| C4 | 1 | — | — | 1 | — | — | — | 1 | — | — |
| C7 | — | 1 | — | 1 | — | — | 1 | — | — | — |
| C8 | — | — | 1 | — | — | 1 | — | — | — | — |
| D5 | — | — | 1 | — | — | — | — | — | — | — |
| D8 | 1 | — | — | — | — | — | — | — | — | — |
| D10 | — | — | 1 | — | — | — | — | — | — | — |
| D13 | — | — | — | — | — | — | 1 | — | — | — |
| D16 | — | 1 | — | — | — | — | — | 1 | 1 | — |
| D17 | — | 1 | — | 1 | — | — | — | — | — | — |
| D19 | — | 1 | 1 | — | — | — | — | — | — | — |
| D20 (OH) | — | — | 1 | — | — | — | 1 | — | — | — |
| D24 | — | — | — | — | — | — | 1 | — | 1 | — |
| D27 | — | 1 | — | — | — | — | — | — | — | — |
| D30 | — | — | 1 | — | — | — | 1 | — | — | |
| D30 (OH) | — | 1 | — | — | — | — | — | — | — | — |

The following symbols denote:
— same aspect as non infected subjects, 1 slight erythema, 2 erythema, 3 erythema + profuse exudate, R urine retention.

II Antiviral Activity of the Compounds of the Invention on Influenza A/Bangkok/79 Virus Infection of Mice A group of Swiss A mice from a closed colony at the university of Sheffield aged 4–5 weeks and weighing approximately 15–20 gms, were divided into groups of 25. Groups were inoculated daily for 6 days, intraperitoneally with compounds under test in an 0.2 ml volume: all the compounds were dissolved in Phosphate Buffered Saline (PBS) containing 0.2% carboxymethylcellulose and 0.2% tween 80. Twentyfour hours after this first drug administration all mice were inoculated intranasally with $10^{5.0}$ $EID_{20}$ of influenza A virus in an 0.05 ml volume of PBS. Three mice from each group were killed at daily intervals for five days after viral inoculation; the lungs were removed, separately ground in PBS containing 2.0% bovine serum albumin to give a 40% suspension, centrifuged at 2000 r.p.m. for 10 mins, and the supernatent fluid titrated by the allantoin-on-shell (AOS) method for infectivity. On completion of the study at day 15, the remaining 10 animals in each group were killed and the lungs scored for consolidation. Preliminary assays have shown that preferred i.p. dose was, for the tested compounds, around 1 mg/kg so this figure was retained in the experiment.

Using the above experimental protocol, 15 groups of 25 mice were given each, one of the compounds of the invention by the intraperitoneal (i.p.) route at the concentration of 1.0 mg/kg in an 0.2 ml volume of phosphate buffered saline (PBS) containing 0.2% carboxymethylcellulose and 0.2% tween 80. A control group of mice were given buffer alone. The compounds were administered once a day for 6 days from 24 hours prior to infection with influenza A/Bangkok/79 virus.

Table 2, left hand part, shows the titres of virus present in the lungs from days 1–5 following virus infection. For untreated mice virus titres increased to a maximum of $10^{2.5}$–$10^{2.9}$ $EBID_{50}$/ml on days 2 and 3, post-inoculation; after this time, the titres declined, but at day 5 the mean titre of virus present in the lung was $10^{1.8}$ $EBID_{50}$/ml.

The degree of lung consolidation following infection of mice with influenza virus A/Bangkok/79 was measured: the lungs from each animal were graded 1 (25% consolidation), 2 (25–50% consolidation), 3 (50–75% consolidation) and 4 (total consolidation); and the mean score of each group of animals is shown in Table 2, right hand part. For control mice the lung consolidation ranged from 2–3 with a mean value of 2.6.

Conclusion

The results show that the compounds of the invention at a concentration of 1.0 mg/kg given i.p. to mice significantly decreased the titres of virus in the lungs and the degree of lung consolidation compared to the results obtained for control animals.

A comparable experiment was conducted but with an oral administration of the compounds of the invention: similar results were obtained at doses, varying with the compound and comprised between 15 and 60 mg/kg.

PRESENTATION—POSOLOGY

The compounds of the invention may be presented under the form of creams or gels, lotions and sprays containing 1 to 5% in weight of active ingredient, dissolved in diethyleneglycol monoethyl ether for topical applications. Usual posology in human therapy comprises 1–4 daily applications. Presentations for oral administration comprise tablets or gelatine capsules in dose units containing 100 mg of active ingredient, associated with an appropriate carrier. Posology, per os, in human therapy is from 1 to 8 dose unit per diem.

TABLE 2

| Days after infection Virus titre in lungs (EBID$_{50}$/ml) on day | | | | | Compounds | Lung Consolidation | |
|---|---|---|---|---|---|---|---|
| 1 | 2 | 3 | 4 | 5 | | Range | Mean |
| | | | | | Control | 2–3 | 2.6 |
| <0.5 | <0.5 | <0.5 | <0.5 | <0.5 | $C_4$ | 1–3 | 1.4 |
| <0.5 | <0.5 | <0.5 | <0.5 | <0.5 | $C_7$ | 1–3 | 1.4 |
| <0.5 | 0.6 | <0.5 | <0.5 | <0.5 | $C_8$ | 1–2 | 1.4 |
| <0.5 | 0.5 | <0.5 | <0.5 | <0.5 | $D_5$ | 1–3 | 1.6 |
| <0.5 | 0.5 | <0.5 | <0.5 | <0.5 | $D_8$ | 1–2 | 1.5 |
| <0.5 | <0.5 | 0.5 | <0.5 | <0.5 | $D_{10}$ | 1–2 | 1.2 |
| <0.5 | 0.5 | 0.5 | <0.5 | <0.5 | $D_{13}$ | 1–3 | 1.3 |
| <0.5 | 0.6 | <0.5 | <0.5 | <0.5 | $D_{16}$ | 1–2 | 1.6 |
| <0.5 | 0.5 | 0.5 | <0.5 | <0.5 | $D_{17}$ | 1–2 | 1.6 |

TABLE 2-continued

| Days after infection Virus titre in lungs (EBID$_{50}$/ml) on day | | | | | Compounds | Lung Consolidation | |
|---|---|---|---|---|---|---|---|
| 1 | 2 | 3 | 4 | 5 | | Range | Mean |
| | | | | | Control | 2–3 | 2.6 |
| <0.5 | <0.5 | 0.5 | <0.5 | <0.5 | $D_{19}$ | 1–2 | 1.2 |
| <0.5 | <0.5 | <0.5 | <0.5 | <0.5 | $D_{20}(OH)$ | 1–2 | 1.2 |
| <0.5 | 0.5 | 0.6 | <0.5 | <0.5 | $D_{24}$ | 1–3 | 1.1 |
| <0.5 | 0.6 | <0.5 | <0.5 | <0.5 | $D_{27}$ | 1–3 | 1.3 |
| <0.5 | 0.6 | <0.5 | <0.5 | <0.5 | $D_{30}$ | 1–2 | 1.6 |
| <0.5 | <0.5 | <0.5 | <0.5 | <0.5 | $D_{30}(OH)$ | 1–3 | 1.1 |

I claim:
1. Pyranoderivatives of the formula:

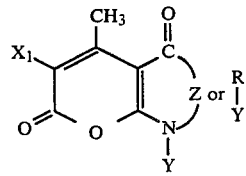

wherein $X_1$ is H, Cl or Br and Z stands for:

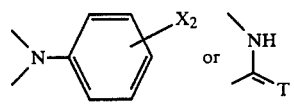

wherein $X_2$ is H, Cl or Br, T is O or S and Y stands for an arabinose, xylose or ribose moiety, the acetylated form of the same, with either a pyranose or furanose configuration and bound to the R moiety of either the $\alpha$ or the $\beta$ anomer.

2. A therapeutic composition comprising an antivirally effective amount of a compound according to claim 1 in a pharamceutically acceptable carrier.

3. A therapeutic composition comprising an antibacterially effective amount of a compound according to claim 1 in a pharmaceutically acceptable carrier.

4. A therapeutic composition comprising an anticardiovascularly effective amount of a compound according to claim 1 in a pharmaceutically acceptable carrier.

* * * * *

UNITED STATES PATENT AND TRADEMARK OFFICE
CERTIFICATE OF CORRECTION

PATENT NO. : 4,704,454
DATED : November 3, 1987
INVENTOR(S) : Andre Esanu

It is certified that error appears in the above-identified patent and that said Letters Patent is hereby corrected as shown below:

Column 2, line 19, change "0.2 1" to --0.27 1--.

Column 4, line 60, change "$C_{18}N_{18}N_2O_7Cl$" to --$C_{18}H_{18}N_2O_7Cl$--.

Column 5, line 50, change "$X_2 = H$" to --$X_1 = H$--.

Column 7, line 61, change "(2,3d)" to --(2,3-d)--.

Column 7, line 62, delete "$X_1 = H$" and insert on line 63 --$X_1 = H$--.

Column 8, line 8, change "(2,3d)" to --(2,3-d)--.

Column 8, line 42, change "(2,3d)" to --(2,3-d)--.

Column 9, line 42, change "(2,3d)" to --(2,3-d)--.

Column 13, line 67, change "similar1" to --similar--.

Column 16, line 40, change "pharamceutically" to --pharmaceutically--.

Signed and Sealed this

Nineteenth Day of April, 1988

Attest:

DONALD J. QUIGG

*Attesting Officer*     *Commissioner of Patents and Trademarks*